(12) United States Patent
Shimizu

(10) Patent No.: US 9,011,343 B2
(45) Date of Patent: Apr. 21, 2015

(54) BIOLOGICAL SIGNAL MEASURING APPARATUS

(75) Inventor: Hideki Shimizu, Nishitokyo (JP)

(73) Assignee: Citizen Holdings Co., Ltd., Tokyo (JP)

( * ) Notice: Subject to any disclaimer, the term of this patent is extended or adjusted under 35 U.S.C. 154(b) by 863 days.

(21) Appl. No.: 12/730,630

(22) Filed: Mar. 24, 2010

(65) Prior Publication Data

US 2010/0249662 A1 Sep. 30, 2010

(30) Foreign Application Priority Data

Mar. 25, 2009 (JP) ................................ 2009-074061

(51) Int. Cl.
| | |
|---|---|
| A61B 5/00 | (2006.01) |
| A61B 5/02 | (2006.01) |
| A61B 5/04 | (2006.01) |
| A61B 5/103 | (2006.01) |
| A61B 5/117 | (2006.01) |
| A61B 5/024 | (2006.01) |
| A61B 5/0452 | (2006.01) |

(52) U.S. Cl.
CPC ........... *A61B 5/02438* (2013.01); *A61B 5/7264* (2013.01); *A61B 5/0452* (2013.01); *A61B 5/7207* (2013.01); *A61B 5/721* (2013.01); *A61B 5/7203* (2013.01); *A61B 5/024* (2013.01); *A61B 5/681* (2013.01)

(58) Field of Classification Search
CPC ...... A61B 5/024; A61B 5/0452; A61B 5/721; A61B 5/7203; A61B 5/7207; A61B 5/7264

USPC ......... 600/300, 306, 500–503, 509, 519, 523, 600/527, 529, 544, 552, 587, 595

See application file for complete search history.

(56) References Cited

U.S. PATENT DOCUMENTS

| | | | | |
|---|---|---|---|---|
| 5,966,684 | A * | 10/1999 | Richardson et al. | 702/191 |
| 6,095,984 | A | 8/2000 | Amano et al. | |
| 7,197,357 | B2 | 3/2007 | Istvan et al. | |
| 7,853,317 | B2 * | 12/2010 | Duann et al. | 600/509 |
| 8,160,703 | B2 * | 4/2012 | Stickney et al. | 607/19 |
| 8,758,258 | B2 * | 6/2014 | Takahashi et al. | 600/483 |

FOREIGN PATENT DOCUMENTS

CN 1195277 A 10/1998

* cited by examiner

*Primary Examiner* — Devin Henson
(74) *Attorney, Agent, or Firm* — The Webb Law Firm

(57) ABSTRACT

A biological signal measuring apparatus that is provided with an oscillatory wave detection apparatus, an oscillatory wave period measuring part, a group memory apparatus that is configured to collect the periodic data and to store the periodic data as a group signal, and a vibration frequency calculation apparatus. The vibration frequency calculation apparatus is provided with a section discrimination part configured to compare the group signal with a predetermined value to carry out a section discrimination, a section memory part configured to store to a plurality of sections, a weight coefficient memory part configured to store a weight coefficient, and an oscillatory wave period weighted average value calculation part.

8 Claims, 12 Drawing Sheets

1 Biological signal measuring apparatus

Fig. 9

| Group | Periodic data Da | Period (arbitrary unit) | Discrimination section | Discrimination standard | Weight coefficient |
|---|---|---|---|---|---|
| Group signal Ga1 | Da3 | 3.6 | A | Da3<das | 1 |
| | Da4 | 4.0 | A | Da4<das | 1 |
| | Da5 | 6.5 | B | das≦Da5<dal | 10 |
| | Da6 | 6.5 | B | das≦Da6<dal | 10 |
| | Da7 | 8.0 | B | das≦Da7<dal | 10 |
| | Da8 | 9.0 | B | das≦Da8<dal | 10 |
| | Da9 | 8.0 | B | das≦Da9<dal | 10 |
| | Da10 | 5.0 | A | Da10<das | 1 |
| | Da11 | 9.0 | B | das≦Da11<dal | 10 |
| | Da12 | 11.5 | C | Da12≧dal | 1 |
| | Da13 | 5.0 | A | Da13<das | 1 |
| | Da14 | 12.0 | C | Da14≧dal | 1 |
| | Da15 | 5.0 | A | Da15<das | 1 |
| | Da16 | 18.5 | C | Da16≧dal | 1 |

Note: das = 3.6 × 1.4 (140%) = 5.04 or dal = 18.5 × 0.5 (50%) = 9.25

BIOLOGICAL SIGNAL MEASURING APPARATUS

TECHNICAL FIELD

The present invention relates to a biological signal measuring apparatus that is configured to measure the number of repetitions per unit time for a periodic oscillatory wave that is generated by a biological body, such as an oscillatory wave that is caused by a pulsation of a biological heart or a breath and a physical oscillatory wave that is generated by walking.

BACKGROUND ART

A biological body generates a wide variety of oscillatory waves having a periodic property in a physiological function and an ecological activity of the biological body, and it is necessary to measure or monitor the number of repetitions per unit time, that is, the vibration frequency for the oscillatory waves more often than not.

For instance, a sports medicine field recommends that a pulse, which is the most basic oscillatory wave that is generated by a biological body, is monitored in a successive manner in order to prevent an accident such as a heart failure and to improve a training effect in the case in which the training is carried out by using the physical exercise support equipment such as an ergometer and a treadmill. Moreover, a lot of people execute a walking to maintain a good health, and a pedometer that is configured to detect an oscillatory wave caused by walking to inform of the number of steps is used at large.

There are a wide variety of oscillatory waves having a periodic property for a biological body. In particular, a pulse that indicates a pulsation of a biological heart is most important and close to one's heart among oscillatory waves having a periodic property. A wide variety of techniques have been proposed for the measuring method of a pulse. The previously existing technology and problems thereof will be described in the following while mainly focusing on a measurement of a pulse.

A measurement of palpation that is carried out by a clinical nurse in a hospital while using a stopwatch is a method that has been adopted through the ages as a measuring method of a pulse. For the measurement of palpation, a pulse wave is sensed by pressing a blood vessel that is close to a thumb on a hand palm side of a wrist with a tip of a finger to sense a generation of a pulse wave for a predetermined time.

However, a certain level of skill is required for the above method, and it is hard to carry out the above method by oneself. Consequently, an apparatus that is configured to electrically measure a pulse wave has been proposed.

A wide variety of apparatuses that are configured to electrically measure a pulse wave have been proposed. In particular, there is widely known a measurement based on a so-called direct counting system in which a pulse wave signal is detected by using a sensor that detects a change of a blood flow in a tip of a finger and the number of pulse wave signals in a minute is counted to be the number of pulses.

However, the direct counting system requires a time period of one minute for a measurement and is not suitable for a continuous measurement of a pulse wave. Consequently, there has been proposed a periodic conversion system in which a time interval of pulse wave signals that have been detected by a sensor, that is, a pulse wave period is calculated, a cumulative value of a pulse wave period that has been obtained by accumulating the pulse wave period by a predetermined number of times is divided by a predetermined number of times to calculate an arithmetic mean value of a pulse wave period, and the arithmetic mean value is converted to pulse waves per minute (see Patent Document 1 for instance).

For the periodic conversion system, a measurement of a pulse wave can be carried out by using a few of pulse wave signals. Moreover, the periodic conversion system is suitable for a continuous measurement of a pulse wave. In the case in which a pulse wave is measured during a physical exercise such as a sport, an error signal of a short period is easily mixed due to a noise caused by a vibration, or a proper pulse wave signal is omitted due to a body motion or the like, whereby an error signal of a long period is generated. As a result, a measured value can vary quite a bit unfortunately.

In order to solve the above problem, there has been proposed a body motion removal system in which a component of a body motion that is contained in a pulse wave signal is removed by using a pulse sensor and a body motion sensor in combination to obtain a pulse wave (see Patent Document 2 for instance).

Moreover, a technique for detecting an electrocardiographic wave has been proposed as another method for preventing a degradation of measurement accuracy due to a body motion noise. For the electrocardiographic wave detection system, since an electrocardiographic wave is stable even in the case in which a body motion is complicated, a measurement during a physical exercise can be carried out. However, a total configuration of an apparatus for the electrocardiographic wave detection system has a tendency to be complicated, and the electrocardiographic wave detection system is not yet widely used as the general technology.

For the previously existing technology that is described in the above Patent Document 2, an improved technique of a composition element that is mainly hardware is disclosed. On the other hand, there also has been proposed a technique for detecting a pulse wave in an accurate fashion by using the signal processing technology that is software (see Patent Document 3 for instance).

For the previously existing technology that is described in the above Patent Document 3, there has been proposed the signal processing technology for improving a degree of accuracy in a measurement of a pulse wave by carrying out a processing for removing a numeric value that cannot be in a range of physiological numeric values in a step for calculating an oscillatory wave from a plurality of pulse wave periods that have been measured.

CITATION LIST

Patent Document

[Patent Document 1]
Japanese Patent Application Laid-Open Publication No. 58-30694 (Claims, FIG. 1)
[Patent Document 2]
Japanese Patent Application Laid-Open Publication No. 2004-298609 (Claims, FIG. 3)
[Patent Document 3]
Japanese Patent Application Laid-Open Publication No. 2006-297004 (Claims, FIG. 1)

SUMMARY OF INVENTION

Technical Problems

For an improved technique by hardware such as a body motion removal system, in addition to a sensor for measuring a pulse wave, an acceleration sensor for detecting a body motion and a peripheral circuit are required separately. Consequently, an apparatus is complicated and a cost tends to be increased.

On the other hand, like the previously existing technology that is described in the above Patent Document 3, in the case in which a degree of accuracy in a measurement is improved by removing a numeric value that cannot be in a range of physiological numeric values (hereafter referred to as a value that cannot be physiologically generated) for the signal processing technology, the technology is effective for a component of a body motion caused by a simple movement of a user and a noise having a periodic component extremely separate from a pulse wave. However, a component that is close to a pulse wave signal cannot be sufficiently removed for a complicated component of a body motion (a body motion noise) in an execution of a sport and a noise having a wide periodic component, whereby a degree of accuracy in a measurement is degraded.

[Descriptions of Problems in a Signal Processing Based on a Well Known Technique: FIG. 6 and FIG. 7]

A pulse wave that is a an oscillatory wave of a biological body and a well known technique for processing a pulse wave signal by using the pulse wave will be described in the following with reference to FIG. 6 and FIG. 7.

FIG. 6 shows an example of a general pulse wave signal of a biological body, and FIG. 7 is a waveform diagram in the case in which the pulse wave signal shown in FIG. 6 is processed by a well known technique.

A waveform p11 that is generated in a cyclic manner in FIG. 6(a) indicates a pulse wave signal measured by a pressure sensor that is disposed close to a radius of a wrist, and a spiny waveform p11n that is generated on an irregular base indicates an electromagnetic or mechanical noise that is mixed from the environment.

A waveform p12 in FIG. 6(b) indicates a noise in which two components that are a slow fluctuation noise that is generated by a breathing operation and a body motion noise having the large amplitude of vibration due to a physical exercise are mixed.

A waveform p1 in FIG. 6(c) is an output waveform of a pressure sensor in the state in which a noise p11n and a noise p12 are added to the waveform p11 caused by a pulse wave, and indicates a state in which an amplitude is extremely dispersed due to an incorporation of a noise and a fluctuation component.

A signal P1 that is shown in FIG. 7(a) is a signal in which a fluctuation component of a low frequency wave has been removed from the waveform p1 shown in FIG. 6(c) by an electronic circuitry method, and is a waveform in which a pulse wave having the dispersed amplitude on an almost flat base line and a spiny noise signal are mixed.

A "prescribed interval" that is shown in FIG. 7(a) and FIG. 7(b) is a range for calculating the number of pulses in a certain period of time from a plurality of pulse wave signals. For instance, the prescribed interval is an interval for a certain period of time such as 10 seconds to 20 seconds. The prescribed interval can be started with any waveform P1 that is measured in a serial manner. The example that is shown in FIG. 7(a) indicates the state in which the prescribed interval is started with a waveform p3s.

A signal P0 of a dotted line that is shown in FIG. 7(a) is a reference value for identifying the waveform P1 as a significant signal.

The waveforms ps1 to psn in a pulsed shape having the constant amplitude shown in FIG. 7(b) are pulse wave signals that have been identified as a significant signal as compared with the reference value P0. The "Da1 to Da16" are intervals between pulse wave signals ps1 to psn, that is, a periodic data Da, and is numeric value data of a periodic signal between pulse wave signals. The example that is shown in FIG. 7(b) indicates that periodic data is composed of 16 data.

FIG. 7(c) indicates that periodic data Da1 to Da16 are processed and as a result a range that is indicated by a "calculation period" is a new range for calculating the number of pulses.

A well known technique is a system in which a pulse wave period of a pulse wave signal shown in FIG. 7(b) is calculated as periodic data Da1 to Da16, 14 data of periodic data Da3 to Da16 that are a data group in the prescribed interval are examined in order of precedence, and "periodic data that cannot be generated physiologically for a human body" such as a short period and a long period is removed. As a result, a new data group that has been thinned out to be measured is formed as shown in the "calculation period" of FIG. 7(c).

For instance, in the case in which the periodic data Da3, Da4, Da10, Da13, and Da15 are short periods, the periodic data Da12, Da14, and Da16 are long periods, and those data are identified as "periodic data that cannot be generated physiologically for a human body", the above 8 periodic data are removed from 14 periodic data Da3 to Da16 that are a data group to be measured, and the data group to be measured is reduced to be 6 periodic data Da5, Da6, Da7, Da8, Da9, and Da11.

In the case in which the number of data is reduced as described above, the number of data may cause a result measurement system to be greatly changed in some cases.

More specifically, for a digital signal processing theory, in the case in which an averaging point, that is, the number of data for calculating an average value is M, an interval for incorporating data, that is, a sample interval is $\Delta t$, a cutoff frequency that has an influence to a frequency response of a measurement system is fc, and C is a constant, a discussion can be carried out based on the following expression.

$$fc \cdot M \cdot \Delta t = C$$

Here, in the case in which fc is tried to be obtained, the expression is fc=C/(M·$\Delta$t).

As described above, since 8 periodic data of a short period and a long period are removed for the well known technique, an averaging point M is reduced from M=14 to M=6, and a frequency band fc is expanded as shown in the following.

Fc=2.33fco (where fco is a frequency band prior to a removal of periodic data)

In the case in which a frequency band is expanded, not only incorporation noises are increased but also a responsibility of a signal is extremely changed disadvantageously.

More specifically, in the case in which all periodic data of a short period and a long period are removed to calculate the number of pulses, as well as all signal components that are contained in the pulse wave signals of a short period and a long period are lost, a frequency characteristic of a measurement system is degraded and noises are increased disadvantageously.

As described above, since the well known technique makes too sharp a distinction between a noise and a signal as 1 or 0, all signal components that are contained in a noise are removed, and all noise components that are contained in a signal are handles as a signal disadvantageously as a basic defect.

As described above, for a signal processing in the well known technique, the special hardware for exclusive use is not necessary. Consequently, although the well known technique has a merit of a low cost, it has to be said that an essential measuring performance is insufficient.

The present invention was made in order to solve the above problems. An object of the present invention is to provide a biological signal measuring apparatus for measuring an oscillatory wave such as a periodic oscillatory wave that is generated by a biological body even in a physical exercise with a high degree of accuracy and at a low cost based on the signal processing technology using software.

Means for Solving the Problems

In order to solve the above problems, a biological signal measuring apparatus in accordance with the present invention is provided with the following configuration.

A biological signal measuring apparatus in accordance with the present invention is a biological signal measuring apparatus configured to detect an oscillatory wave that is generated by a biological body and to calculate data of the vibration frequency per unit time, and is characterized by comprising:

an oscillatory wave detection means configured to detect an oscillatory wave that is generated by a biological body and to output an oscillatory wave signal;

an oscillatory wave period measuring part configured to measure a time interval of the oscillatory wave signals and to output periodic data;

a group memory means configured to collect a plurality of the periodic data and to store the plurality of the periodic data as a group signal that is a data group to be measured; and a vibration frequency calculation means configured to calculate data of the vibration frequency based on the group signal that has been stored into the group memory means.

A biological signal measuring method in accordance with the present invention is a biological signal measuring method for detecting an oscillatory wave that is generated by a biological body and for calculating data of the vibration frequency per unit time, and is characterized by comprising:

an oscillatory wave signal generation step for detecting an oscillatory wave that is generated by a biological body and for generating an oscillatory wave signal;

an oscillatory wave period data generation step for generating periodic data from a time interval of the oscillatory wave signals;

a group signal generation step for collecting a plurality of the periodic data and for generating a group signal that is a data group to be measured; and a vibration frequency calculation step for calculating data of the vibration frequency based on the group signal.

The biological signal measuring apparatus in accordance with the present invention is characterized by comprising the vibration frequency calculation means comprising:

a section discrimination part configured to input the plurality of periodic data that configure the group signal and to compare the plurality of periodic data and a length of a predetermined periodic signal to carry out a section discrimination;

a section memory part configured to store the plurality of periodic data to which a section discrimination has been carried out by the section discrimination part for each section and to output section data for a plurality of sections;

a weight coefficient memory part configured to store a plurality of weight coefficients corresponding to the plurality of section data; and an oscillatory wave period weighted average value calculation part configured to calculate an oscillatory wave period weighted average value from the plurality of section data and the plurality of weight coefficients corresponding to the section data, wherein data of the vibration frequency is calculated based on the oscillatory wave period weighted average value.

The biological signal measuring method in accordance with the present invention is characterized by comprising the vibration frequency calculation step comprising:

a section discrimination step for comparing the plurality of periodic data and a length of a predetermined periodic signal to carry out a section discrimination based on the plurality of periodic data that configure the group signal;

a section data generation step for generating section data for a plurality of sections based on the plurality of periodic data to which a section discrimination has been carried out in the section discrimination step; and an oscillatory wave period weighted average value calculation step for calculating an oscillatory wave period weighted average value from the plurality of section data and a plurality of weight coefficients corresponding to the plurality of section data, wherein data of the vibration frequency is calculated based on the oscillatory wave period weighted average value.

The biological signal measuring apparatus in accordance with the present invention is characterized in that the section discrimination part is configured to calculate a length of the predetermined periodic signal based on the plurality of periodic data.

The biological signal measuring apparatus in accordance with the present invention is characterized by further comprising an indication means configured to indicate the data of the vibration frequency.

The biological signal measuring apparatus in accordance with the present invention is characterized in that all periodic data are rewritten for an update in the case in which a group signal that is stored into the group memory means is updated.

The biological signal measuring apparatus in accordance with the present invention is characterized in that a part of periodic data is rewritten for an update in the case in which a group signal that is stored into the group memory means is updated.

The biological signal measuring apparatus in accordance with the present invention is characterized in that the oscillatory wave is a pulse wave that is generated by the pulsation of a heart, an electrocardiographic wave that indicates an electrical activity of a heart, a skin oscillatory wave that is generated by a breath, an oscillatory wave in walking, or a brain wave.

Advantageous Effects of Invention

By the present invention, a plurality of the periodic data that is a time interval of an oscillatory wave signal such as a pulse wave are collected and stored as a group signal that is a data group to be measured. The periodic data is compared with a predetermined value by a section discrimination part and classified into a plurality of sections such as a section of a short period, a section of a middle period, and a section of a long period. A weight coefficient is increased for the periodic data of a middle period, and a weight coefficient is decreased for the periodic data of a short period and the periodic data of a long period to calculate an oscillatory wave period weighted average value.

In other words, the proper periodic data that is most included in a section of a middle period is weighted with a high weight coefficient. On the other hand, the periodic data that includes a noise and that is included in a section of a short period or a section of a long period with a great deal is not removed at all and is weighted with a low weight coefficient.

Consequently, in handling a signal and a noise, a distinction is not made too sharp between a signal and a noise as 1 or 0, and a signal and a noise are individually weighted sensitively in detail. As a result, a reduction in the number of data to be measured does not cause a frequency band to be expanded, whereby it is possible to provide a biological signal measuring apparatus having a high degree of accuracy at a low cost.

BRIEF DESCRIPTION OF THE DRAWINGS

FIG. 9 is a table showing a numeric value example of an oscillatory wave signal for a first embodiment of a biological signal measuring apparatus in accordance with the present invention.

MODE FOR CARRYING OUT THE INVENTION

A general operation of the biological signal measuring apparatus in accordance with the present invention is to incorporate a plurality of oscillatory waves that are generated by a biological body and to rearrange and rank the oscillatory waves according to a length of the period.

The periods of oscillatory waves that have been rearranged are classified into sections. For instance, an oscillatory wave having a short period and an oscillatory wave having a long period are considered to possess lower reliability, and an oscillatory wave having a middle period is considered to possess higher reliability. The sections (tree sections in this case) are then weighted.

Weighting of a section that is considered to possess lower reliability is weakened, and weighting of a section that is considered to possess higher reliability is strengthened. The weighted average thereof is then obtained.

By the above steps, an oscillatory wave that is considered to possess higher reliability can be used even in the case in which a period of a vibration frequency is dispersed.

In the case in which an oscillatory wave is a pulse wave of a human body, a signal processing of a proper pulse wave (not a noise) can be carried out, whereby an accuracy of a calculation of a heart rate can be improved.

Such an operation will be described in detail in the following.

The periodic data of a plurality of oscillatory waves that are generated by a biological body are collected as a group signal, each of periodic data is compared with a length of a predetermined periodic signal (a threshold value) to carry out a section discrimination, the periodic data is stored for each section as the section data, a weight coefficient is stored for each section, an oscillatory wave period weighted average value of the periodic data is calculated from the section data and the weight coefficient, and the data of the vibration frequency per unit time is calculated to be displayed. Moreover, after the data of the vibration frequency is calculated to be displayed, the group signal that has been used for the calculation is updated.

An embodiment (example) of the biological signal measuring apparatus in accordance with the present invention will be described below in detail with reference to the drawings. In the descriptions, an oscillatory wave that is generated by a biological body is explained as a pulse wave. Moreover, in order to measure the pulse wave, the biological signal measuring apparatus is worn on a wrist of a human body for instance.

Figure 1:
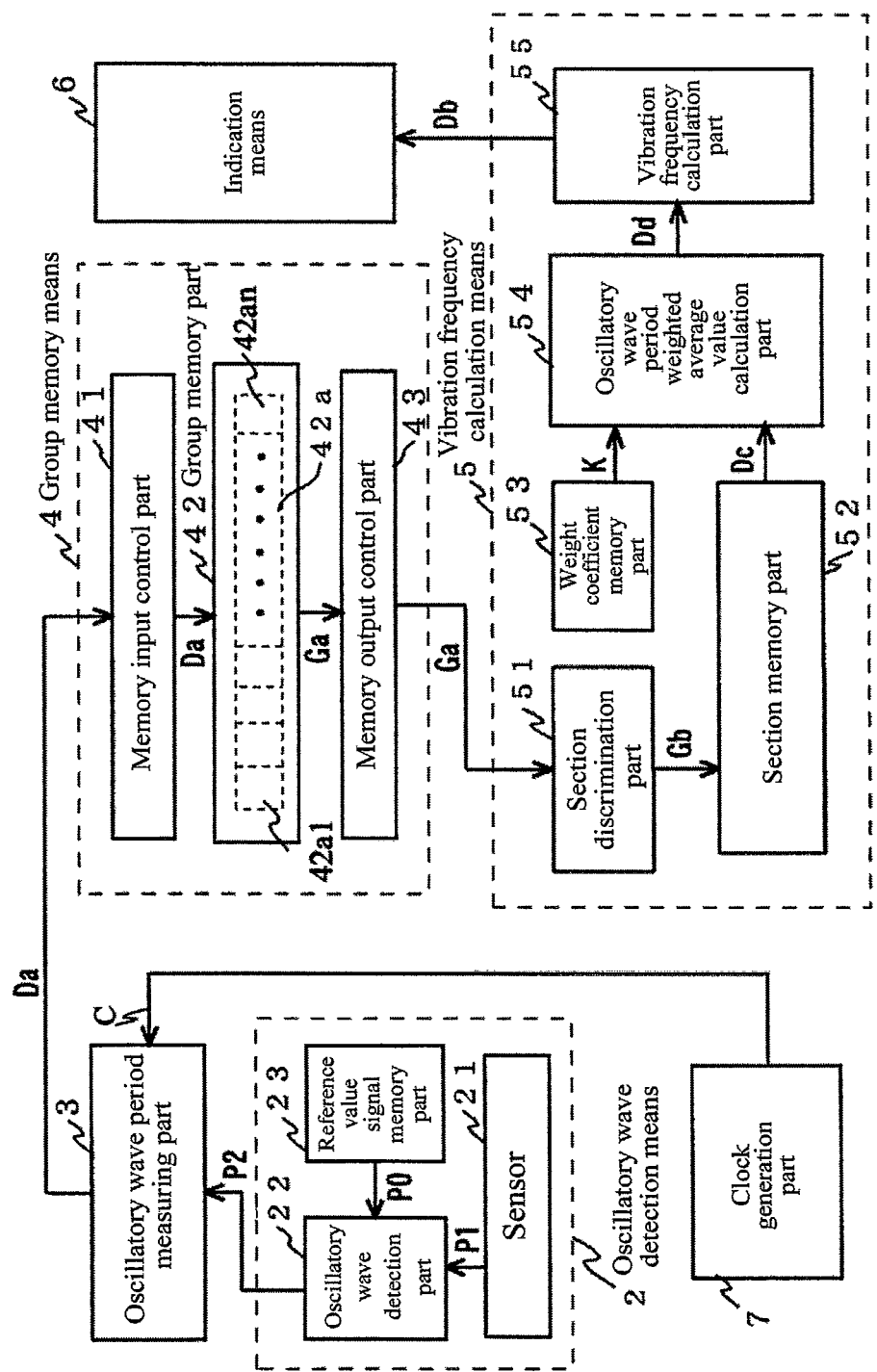
FIG. 1 is a functional block diagram showing a first embodiment of a biological signal measuring apparatus in accordance with the present invention.
Figure 8:
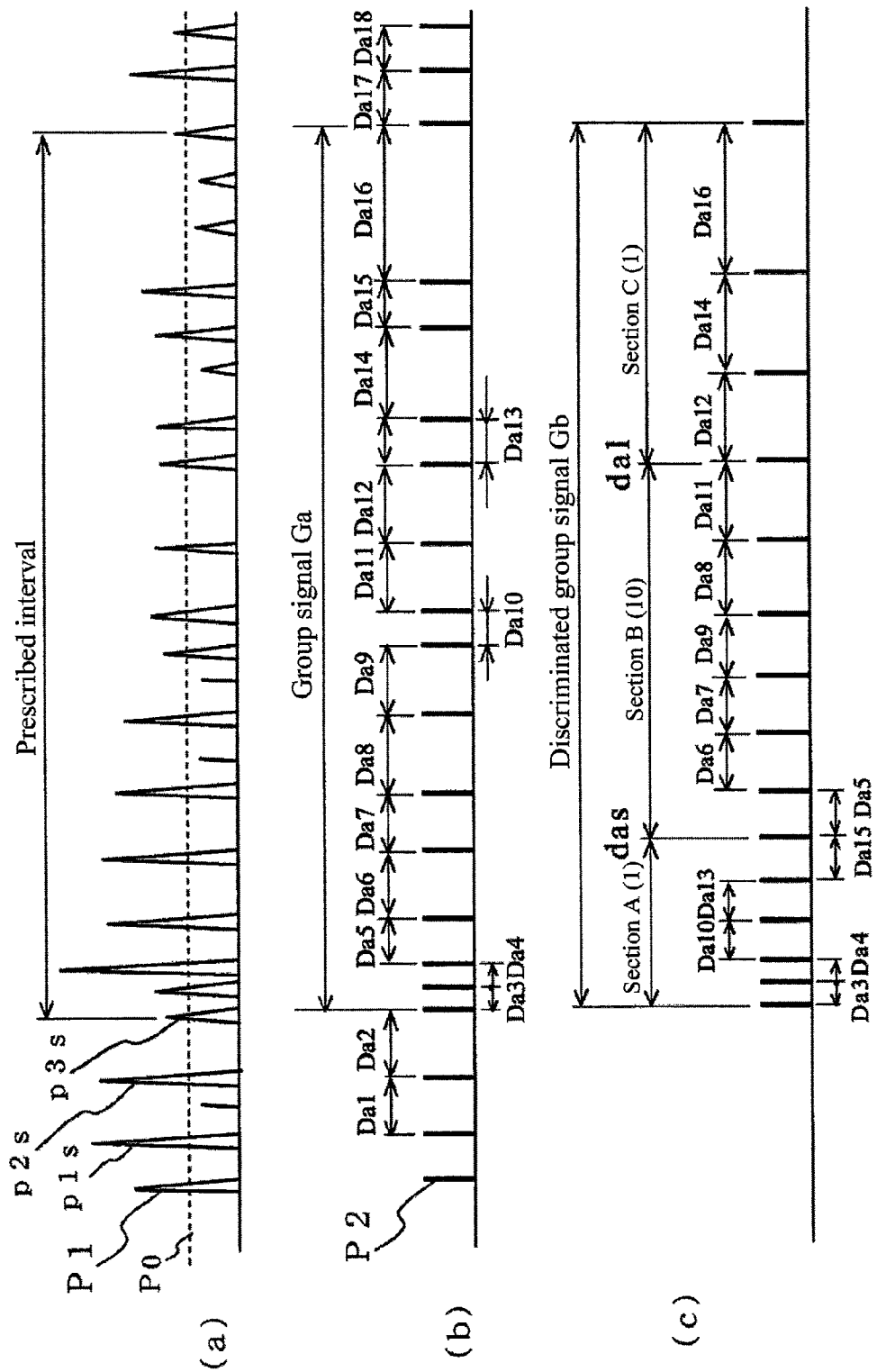
FIG. 8 is a waveform diagram of an oscillatory wave for a first embodiment of a biological signal measuring apparatus in accordance with the present invention.

[Embodiment 1]
[Descriptions of all Drawings for a First Embodiment: FIG. 1 and FIG. 8]

A first embodiment (example) of the biological signal measuring apparatus in accordance with the present invention will be described below in detail with reference to FIG. 1 and FIG. 8.

FIG. 1 is a functional block diagram, FIG. 8 is a waveform diagram of an oscillatory wave signal, and FIG. 9 is a table showing a numeric value example of an oscillatory wave signal.

A configuration of the first embodiment of the biological signal measuring apparatus in accordance with the present invention will be described below in detail with reference to FIG. 1 and FIG. 8.

In FIG. 1, a biological signal measuring apparatus 1 is composed of an oscillatory wave detection means 2, an oscillatory wave period measuring part 3, a group memory means 4, a vibration frequency calculation means 5, an indication means 6, and a clock generation part 7.

[Descriptions of the Oscillatory Wave Detection Means 2: FIG. 1 and FIG. 8]

The oscillatory wave detection means 2 will be described in the first place.

The oscillatory wave detection means 2 is composed of a sensor 21, an oscillatory wave detection part 22, and a reference value signal memory part 23, and is configured to output an oscillatory wave signal P2.

A pressure sensor can be used as the sensor 21 although it is not restricted in particular. For instance, the sensor 21 detects an oscillatory wave (a pulse wave) based on a pulsing motion of a radial artery. A signal processing of the pulse wave is carried out to output a sensor signal P1.

As described above, a pulse wave is measured as a waveform that is generated in a cyclic manner, and a spiny waveform that is generated on an irregular base is mixed to the signal as an electromagnetic or mechanical noise. A waveform of a pulse wave contains a noise in which two components that are a slow fluctuation noise that is generated by a breathing operation and a body motion noise having the large amplitude of vibration due to a physical exercise are mixed, and amplitude is dispersed. A sensor signal P1 that is shown in FIG. 8(a) is a signal in which a fluctuation component of a low frequency wave has been removed by an electronic circuitry method, and is a waveform in which a pulse wave having the dispersed amplitude on an almost flat base line and a spiny noise signal are mixed.

The reference value signal memory part 23 stores a threshold value for distinguishing a signal and a noise, and is configured to output a reference value signal P0.

The reference value signal P0 is a reference value for identifying the sensor signal P1 as a significant signal. More specifically, the reference value signal P0 is a value that is a threshold value for judging with a size of a signal (a signal level) whether or not an oscillatory wave that has been measured is an oscillatory wave based on a pulsing motion of a radial artery. For instance, in the case in which an oscillatory wave that has been measured is too weak, the reference value signal P0 is a material for judging that the oscillatory wave that has been measured is not an oscillatory wave. The reference value signal P0 described above can be determined to be in the range of 10 to 20% of the maximum value of the sensor signal P1 by an experiment or the like in advance.

The sensor signal P1 and the reference value signal P0 are input to the oscillatory wave detection part 22, and the oscillatory wave detection part 22 outputs an oscillatory wave signal P2.

The sensor signal P1 and the reference value signal P0 are compared with each other as shown in FIG. 8(a), and the sensor signal P1 having amplitude that is larger than that of the reference value signal P0 is output as the oscillatory wave signal P2 as shown in FIG. 8(b).

[Descriptions of the Oscillatory Wave Period Measuring Part 3: FIG. 1 and FIG. 8]

The oscillatory wave period measuring part 3 will be described in the next place.

A clock signal C that is output from the clock generation part 7 and the oscillatory wave signal P2 that is output from the oscillatory wave detection means 2 are input to the oscillatory wave period measuring part 3, and the oscillatory wave period measuring part 3 outputs a periodic data Da.

The clock signal C is a reference clock signal for measuring a time interval of the oscillatory wave signal P2, and can be generated by a well known clock generation means that includes a crystal oscillator, an oscillation circuit, and a frequency dividing circuit.

The periodic data Da is data that is obtained by calculating a time interval of the oscillatory wave signal P2, that is, a period of an oscillatory wave as shown in FIG. 8(b), and is composed of 16 data of Da1 to Da16 for the example shown in FIG. 8(b). The number of periodic data is not restricted to 16.

[Descriptions of the Group Memory Means 4: FIG. 1 and FIG. 8]

The group memory means 4 will be described in the next place.

The group memory means 4 is composed of a memory input control part 41, a group memory part 42, and a memory output control part 43. The periodic data Da is input from the oscillatory wave period measuring part 3 to the group memory means 4, and the group memory means 4 outputs a group signal Ga. The configuration of the group memory means 4 will be described in detail in the following.

The memory input control part 41 stores a plurality of periodic data Da of a "prescribed interval" that is output from the oscillatory wave period measuring part 3 into a plurality of memory cells 42a of the group memory part 42 in the order of time series.

The "prescribed interval" is a range for calculating the number of pulses in a certain period of time from a plurality of sensor signals P1. For instance, the prescribed interval is an interval for a certain period of time such as 10 seconds to several tens seconds. The prescribed interval can be started with any sensor signal P1 calculated from a pulse wave that has been measured in a serial manner. The example that is shown in FIG. 8(a) indicates the state in which the prescribed interval is started with a waveform p3s next to a waveform p2s next to a waveform p1s. As a matter of course, any time can be selected for the prescribed interval.

The group memory part 42 is provided with a plurality of memory cells 42a1 to 42an in order to store the periodic data Da1 to Da16 that are a plurality of data in the order of time series. For instance, in the case in which the periodic data Da is composed of 16 data and all of the 16 data is included in the "prescribed interval", the group memory part 42 is provided with a memory cell 42a in which at least the 16 data can be input.

For instance, the periodic data Da1 is stored into a memory cell 42a1, the periodic data Da2 is stored into a memory cell 42a2, and the periodic data Da16 is stored into a memory cell 42a16. In other words, the periodic data Da is stored into a memory cell 42a in number order. A group of the periodic data Da that have been stored is stored as a group signal Ga.

The group memory part 42 can have a configuration of a ring buffer that is well known. The ring buffer is provided with a plurality of memory cells. In the case in which some of new data are stored into the ring buffer that is a memory, oldest data is eliminated in order from the memory. In the case in which such a type of a memory is used, it is not necessary that the number of memory cells is equivalent to that of periodic data that are incorporated.

As shown in FIG. 8(a), since the periodic data is incorporated as the "prescribed interval" from the waveform p3s, the number of periodic data is 14 of periodic data Da3 to Da16.

The periodic data that has been selected by the "prescribed interval" is stored into the group memory part 42 as a group signal Ga to be measured.

As a matter of course, the "prescribed interval" can be started at any timing. As shown in FIG. 8(b), the periodic data that is incorporated in the group signal Ga is not always Da1 and Da2.

The memory output control part 43 outputs the group signal Ga to the vibration frequency calculation means 5, and then deletes the group signal Ga that has stored into the memory cell 42a of the group memory part 42.

[Descriptions of the Vibration Frequency Calculation Means 5: FIG. 1 and FIG. 8]

The vibration frequency calculation means 5 will be described in the next place.

The vibration frequency calculation means 5 is composed of a section discrimination part 51, a section memory part 52, a weight coefficient memory part 53, an oscillatory wave period weighted average value calculation part 54, and a vibration frequency calculation part 55. The vibration frequency calculation means 5 outputs the vibration frequency data Db based on a group signal Ga that is output from the memory output control part 43 of the group memory means 4.

A signal processing of the vibration frequency calculation means 5 will be described below in detail with reference to FIG. 8.

As shown in FIG. 8(c), the section discrimination part 51 compares a plurality of periodic data Da3 to Da16 that are composition elements of the group signal Ga with the predetermined lengths das and dal of a periodic signal to carry out a section discrimination, and outputs a discriminated group signal Gb.

More specifically, a section discrimination of the group signal Ga shown in FIG. 8(b) is carried out to be a "section A", a "section B", and a "section C" based on a period that is represented as "das" and "dal" as shown in FIG. 8(c). The group signal Ga is rearranged as the discriminated group signal Gb, and is output from the section discrimination part 51 of FIG. 1.

For the predetermined lengths das and dal of a periodic signal, 140% of the minimum period of the periodic data Da3 to Da16 is defined as das and 50% of the maximum period of the periodic data Da3 to Da16 is defined as dal for instance.

More specifically, the periodic data Da having a period equivalent to or less than a length das of a periodic signal (a periodic data Dan<a length das of a periodic signal) is classified as a section A of a short period section, the periodic data Da having a period equivalent to or larger than a length dal of a periodic signal (a periodic data Dan≥a length dal of a periodic signal) is classified as a section C of a long period section, and the periodic data Dan having a period equivalent to or larger than a length das of a periodic signal and less than a length dal of a periodic signal (a length das of a periodic signal≤a periodic data Dan<a length dal of a periodic signal) is classified as a section B of a middle period section In other words, for the example shown in FIG. 8(c), the periodic data Da is discriminated in the order of Da3, Da4, Da10, Da13, Da15, Da5, Da6, Da7, Da9, Da8, Da11, Da12, Da14, and Da16. The section discrimination is carried out for the periodic data Da3, Da4, Da10, Da13, and Da15 in the section A. Similarly, the section discrimination is carried out for the periodic data Da5, Da6, Da7, Da9, Da8, and Da11 in the section B, and the section discrimination is carried out for the periodic data Da12, Da14, and Da16 in the section C.

Although the two predetermined lengths das and dal of a periodic signal is used in the present embodiment, the present invention is not restricted to the configuration. For instance, in the case in which a biological signal measuring apparatus in accordance with the present invention is used for measuring a pulse wave of a human body, at least one predetermined length of a periodic signal can be used corresponding to a size of a fluctuation of a heart rate that is anticipated.

More specifically, in the case in which a light physical exercise such as a walking is carried out (in the case in which a fluctuation of a heart rate is small) for instance, two predetermined periodic signals are used to configure three sections as described above. Moreover, in the case in which a heavy physical exercise such as a running is carried out (in the case in which a fluctuation of a heart rate is large), three predetermined periodic signals can be used to carry out a section discrimination by configuring four sections. On the other hand, in the case in which a pulse wave is measured in a complete rest state (in the case in which a fluctuation of a heart rate hardly occurs), one predetermined periodic signal can be used to carry out a section discrimination by configuring two sections.

As described above, the number of sections to which the section discrimination is carried but is indicated by the following expression:

Number of sections=(number of predetermined periodic signals)+1

Moreover, a lot of predetermined lengths of a periodic signal can also be prepared to use predetermined lengths of the required number of a periodic signal corresponding to a type of a physical exercise for instance.

The section memory part 52 stores the discriminated group signal Gb to which the section discrimination has been carried out by the section discrimination part 51 for a plurality of sections (three sections in this example), and outputs a plurality of section data Dc corresponding to each section. In other words, the section data Dca is output for the section A, the section data Dcb is output for the section B, and the section data Dcc is output for the section C.

More specifically, as shown in FIG. 8(c), 14 periodic data Da of periodic data Da3 to Da16 are as follows:

Section A: section data Dca=[Da3, Da4, Da10, Da13, Da15]

Section B: section data Dcb=[Da5, Da6, Da1, Da9, Da8, Da11]

Section C: section data Dcc=[Da12, Da14, Da16]

The weight coefficient memory part 53 stores a weight coefficient K for a plurality of sections (tree sections in this example), and outputs a plurality of weight coefficients K corresponding to each section. The weight coefficient memory part 53 stores a weight coefficient corresponding to a quality as a signal of each section, such as "1" of a weight coefficient Ka of the section A, "10" of a weight coefficient Kb of the section B, and "1" of a weight coefficient Kc of the section C.

The weight coefficient K for a plurality of sections that has been stored into the weight coefficient memory part 53 is "1" for a weight coefficient Ka, "10" for a weight coefficient Kb, and "1" for a weight coefficient Kc in the above example. However, the present invention is not restricted to this example. The weight coefficient K can be changed as needed corresponding to a characteristic of an anticipated signal to be measured. For instance, in the case in which a biological signal measuring apparatus in accordance with the present invention is used for measuring a pulse wave of a human body, a deviation of the weight coefficient K can be defined corresponding to a size of a body motion noise that is anticipated.

More specifically, in the case in which a light physical exercise such as a walking is carried out (in the case in which a body motion noise is small) for instance, a deviation of the weight coefficient K can be made small. On the other hand, in the case in which a heavy physical exercise such as a running is carried out (in the case in which a body motion noise is large), a deviation of the weight coefficient K can be made large.

The weight coefficient memory part 53 can store the weight coefficients K for sections of a plurality of groups corresponding to a type of a physical exercise for instance. In the case in which such a configuration is adopted, a group of weight coefficients K to be used can be switched corresponding to a type of a physical exercise.

In FIG. 8(c), the weight coefficients are represented as "section A (1)", "section B (10)", and "section C (1)".

As shown in FIG. 8(c), the discriminated group signal Gb is a result of a discrimination of the group signal Ga due to a comparison with the predetermined lengths das and dal of a periodic signal, and is not the information on a real time base. Consequently, it is not appropriate in a precise sense to show FIG. 8(c) in a manner combined with FIG. 8(a) and FIG. 8(b). However, in order to make the descriptions to be understood more easily, FIG. 8(c) is daringly combined with FIG. 8(a) and FIG. 8(b) to be shown.

FIG. 9 is a table showing the result in which a numerical conversion of the periodic data Da3 to Da16 shown in FIG. 8(c) has been carried out by the section discrimination part 51, the section memory part 52, and the weight coefficient memory part 53.

More specifically, a group signal Ga that includes the periodic data Da is shown for the "Group" shown in the table of FIG. 9. The periodic data Da3 to Da16 are shown for the "periodic data Da" in the order of generation. In order to relatively figure out a length of a period of the periodic data Da3 to Da16, numeric values without a physical unit of description are listed after a rounding processing for the "Period (arbitrary unit)".

For the "Discrimination section" shown in the table of FIG. 9, a section of each of the periodic data Da3 to Da16 that configure the group signal Ga is shown based on the result of a discrimination that has been carried out by the section discrimination part 51. A standard of the discrimination is shown for the "Discrimination standard".

A weight coefficient that is stored by the weight coefficient memory part 53 for each section is shown for the "Weight coefficient".

In the table shown in FIG. 9 for instance, the minimum value of the periodic data Da is 3.6 of the periodic data Da3, and the maximum value of the periodic data Da is 18.5 of the periodic data Da16.

As described earlier, the predetermined lengths das and dal of a periodic signal are 140% of the minimum period and 50% of the maximum period, respectively. Consequently, the predetermined lengths das and dal are represented by the following expressions:

$$das=3.6\times1.4=5.04$$

$$dal=18.5\times0.5=9.25$$

In other words, for the periodic data Da3 to Da16, a section is discriminated as a section A in the case in which the periodic data Da is less than 5.04, a section is discriminated as a section B in the case in which the periodic data Da is equivalent to or larger than 5.04 and is less than 9.25, and a section is discriminated as a section C in the case in which the periodic data Da is equivalent to or larger than 9.25.

For instance, since the periodic data Da4 is 4.0, the section discrimination part 51 discriminates a section as the section A. In addition, the weight coefficient memory part 53 specifies and stores a weight coefficient as "1".

Moreover, since the periodic data Da9 is 8.0, the section discrimination part 51 discriminates a section as the section B. In addition, the weight coefficient memory part 53 specifies and stores a weight coefficient as "10".

Furthermore, since the periodic data Da12 is 11.5, the section discrimination part 51 discriminates a section as the section C. In addition, the weight coefficient memory part 53 specifies and stores a weight coefficient as "1".

Similarly, all of sections and weight coefficients for the periodic data Da3 to Da16 are decided.

The oscillatory wave period weighted average value calculation part 54 inputs both of a section data Dc that is output from the section memory part 52 and a weight coefficient K that is output from the weight coefficient memory part 53 for each section, and outputs an oscillatory wave period weighted average value Dd. The oscillatory wave period weighted average value Dd can be obtained by the following expression 1.

$Dd$=(Sum of "weighted periods" of the section data $Dc$)/("the number of weighted data" of the section data $Dc$) [Expression 1]

Here, the sum of the periodic data Da of the section A data Dca is XA, the sum of the periodic data Da of the section B data Dcb is XB, and the sum of the periodic data Da of the section C data Dcc is XC.

Moreover, the number of data of the section A data Dca is XAn, the number of data of the section B data Dcb is XBn, and the number of data of the section C data Dcc is XCn.

In the case in which a weight coefficient of the section A is Ka, a weight coefficient of the section B is Kb, and a weight coefficient of the section C is Kc, the above described expression 1 can be rewritten as shown by the following expression 2.

$Dd=(XAKa+XBKb+XCKc)/(XAnKa+XBnKb+XCnKc)$ [Expression 2]

The vibration frequency calculation part 55 inputs an oscillatory wave period weighted average value Dd that is calculated by the oscillatory wave period weighted average value calculation part 54, and outputs the vibration frequency data Db. The vibration frequency data Db can be obtained by the following expression 3.

Vibration frequency data $Db$=(unit time)/(oscillatory wave period weighted average value $Dd$) [Expression 3]

The indication means 6 displays the vibration frequency data Db that is output from the vibration frequency calculation part 55 of the vibration frequency calculation means 5. Although the indication means 6 is not restricted in particular, a known liquid crystal display device can be used as the indication means 6.

A sequence of processing operations described above can also be repeated. In the case in which a user repeats a measurement of a pulse wave and a new oscillatory wave signal P2(2) is generated, the oscillatory wave period measuring part 3 measures a time interval of the new oscillatory wave signal P2(2) from the oscillatory wave signal P2(2) and a clock signal C, and outputs a new plurality of periodic data Da(2) in a serial manner.

A new signal is represented as a second signal in parentheses, such as an oscillatory wave signal P2(2) as a matter of practical convenience.

In the next place, in the case in which the new periodic data Da(2) is output from the oscillatory wave period measuring part 3, the memory input control part 41 of the group memory means 4 stores the new periodic data Da(2) into the memory cell 42a of the group memory means 4 in the order of time series similarly to the case of the first periodic data, and stores a plurality of periodic data Da(2) in a prescribed interval as a second group signal Ga(2).

The memory output control part 43 of the group memory means 4 outputs the second group signal Ga (2) to the vibration frequency calculation means 5. The vibration frequency calculation means 5 then calculates the second vibration frequency data Db(2) by a weighted average that will be described later based on the second group signal Ga. Moreover, the indication means 6 displays the second vibration frequency data Db(2).

As described above, every time when an oscillatory wave signal P2 is generated due to an oscillatory wave of a user, the new periodic data Da(n), a new group signal Ga(n), and the new vibration frequency data Db(n) are calculated in order of precedence, and the vibration frequency data Db(n) is displayed by the indication means 6.

[Detailed Description of Advantageous Effects of the Invention]

Here, the advantageous effects of the first embodiment described above will be summarized with reference to the table of FIG. 9.

As described above, the oscillatory wave period weighted average value calculation part 54 of the vibration frequency calculation means 5 calculates the oscillatory wave period weighted average value Dd by the expression 2.

As shown in the table of FIG. 9,
the number of data of the section A is XAn=5, and a weight coefficient of the section A is Ka=1,
the number of data of the section B is XBn=6, and a weight coefficient of the section B is Kb=10, and
the number of data of the section C is XCn=3, and a weight coefficient of the section C is Kc=1.

Consequently, the expression 2 is calculated like the expression 3. In other words, $$Dd=(XA+10XB+XC)/(5+60+3)=(XA+10XB+XC)/68$$

In the case in which the above results are compared with the simple average method that has been used so often as not, the results are indicated by the following expressions. In other words, the simple average value according to the simple average method of the group signal Ga to be measured is as follows:

$$XA=Da3+Da4+Da10+Da13+Da15$$

$$XB=Da5+Da6+Da7+Da8+Da9+Da11$$

$$XC=Da12+Da14+Da16$$

By using this, the simple average value can be represented as follows:

$$\text{Simple average value}=(XA+XB+XC)/14$$

For an evaluation, the following table 1 shows a comparison of the contribution to a calculated result of XA, XB, XC in the case of the present invention and the case of the simple average method in the case in which:
sum of the periodic data Da of the section A=XA,
sum of the periodic data Da of the section B=XB, and
sum of the periodic data Da of the section C=XC.

TABLE 1

| Contribution to a calculated result of each section | Sum of the section A (XA) | Sum of the section B (XB) | Sum of the section C (XC) |
| --- | --- | --- | --- |
| Simple average method | 1/14 | 1/14 | 1/14 |
| Present invention | 1/68 | 10/68 | 1/68 |

In other words, although a contribution to a calculated result of a sum XB of the periodic data Da of the section B having a high possibility of including the periodic data Da of a high quality is 1/14 in the simple average method, the contribution in accordance with the present invention is increased to be 10/68.

Moreover, a contribution to a calculated result of a sum XA of the periodic data Da of the section A having a high possibility of including the periodic data Da of a low quality such as an incorporation of a noise and a lack of an oscillatory wave signal P2 and a calculated result of a sum XC of the periodic data Da of the section C have been 1/14 conventionally. However, the contribution in accordance with the present invention is decreased to be 1/68. Consequently, it is found that a distinction of a proper signal and a noise can be more clarified, and an accuracy of a measurement of a vibration frequency can be improved.

Figure 2:
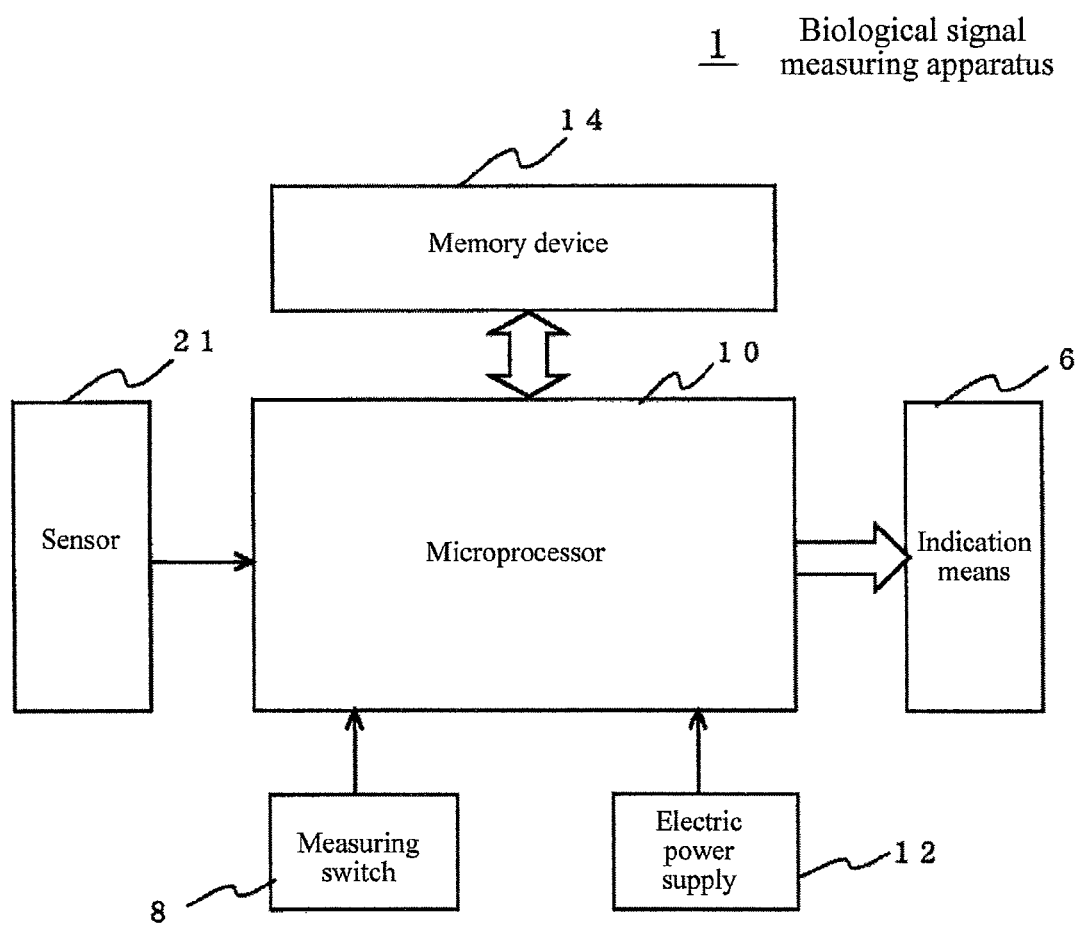
FIG. 2 is a circuit block diagram showing a first embodiment of a biological signal measuring apparatus in accordance with the present invention.

[Descriptions of a Circuit Block: FIG. 2]

The circuit configuration of the first embodiment shown in FIG. 1 will be described with reference to FIG. 2 in the next place.

In FIG. 2, the biological signal measuring apparatus 1 is composed of a sensor 21, a measuring switch 8, a memory device 14, an indication means 6, a microprocessor 10, and an electric power supply 12.

The sensor 21 converts an oscillatory wave having a periodic property for a biological body such as a pulsing motion of a radial artery into a sensor signal P1 and inputs the sensor signal P1 to the microprocessor 10. The measuring switch 8 starts or halts an operation of the biological signal measuring apparatus 1.

The memory device 14 is a memory means such as the reference value signal memory part 23, the group memory means 4, the section memory part 52, and the weight coefficient memory part 53. The memory device 14 is also provided with a memory function of data and a fixed value, which are necessary for an arithmetic processing, and is composed of memory elements that can carry out electrically writing and erasing. A nonvolatile memory device such as an EEPROM can be used for instance.

The indication means 6 is configured by a liquid crystal display device for instance. The indication means 6 indicates the vibration frequency data Db.

The microprocessor 10 controls the entire operation of the biological signal measuring apparatus 1, and assumes a main function of inputting a sensor signal P1 and outputting the vibration frequency data Db. The electric power supply 12 is a drive power supply such as an electric battery for driving the biological signal measuring apparatus 1.

Figure 3:
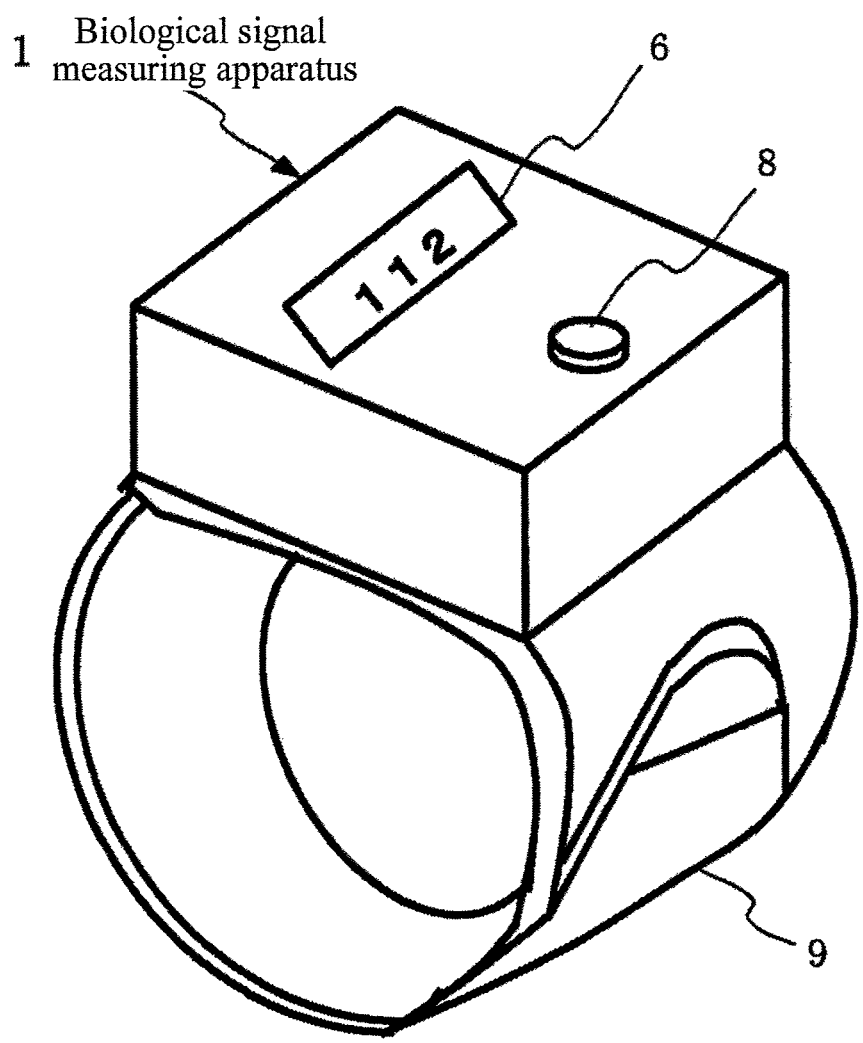
FIG. 3 is an outline view showing a first embodiment of a biological signal measuring apparatus in accordance with the present invention.
Figure 4:
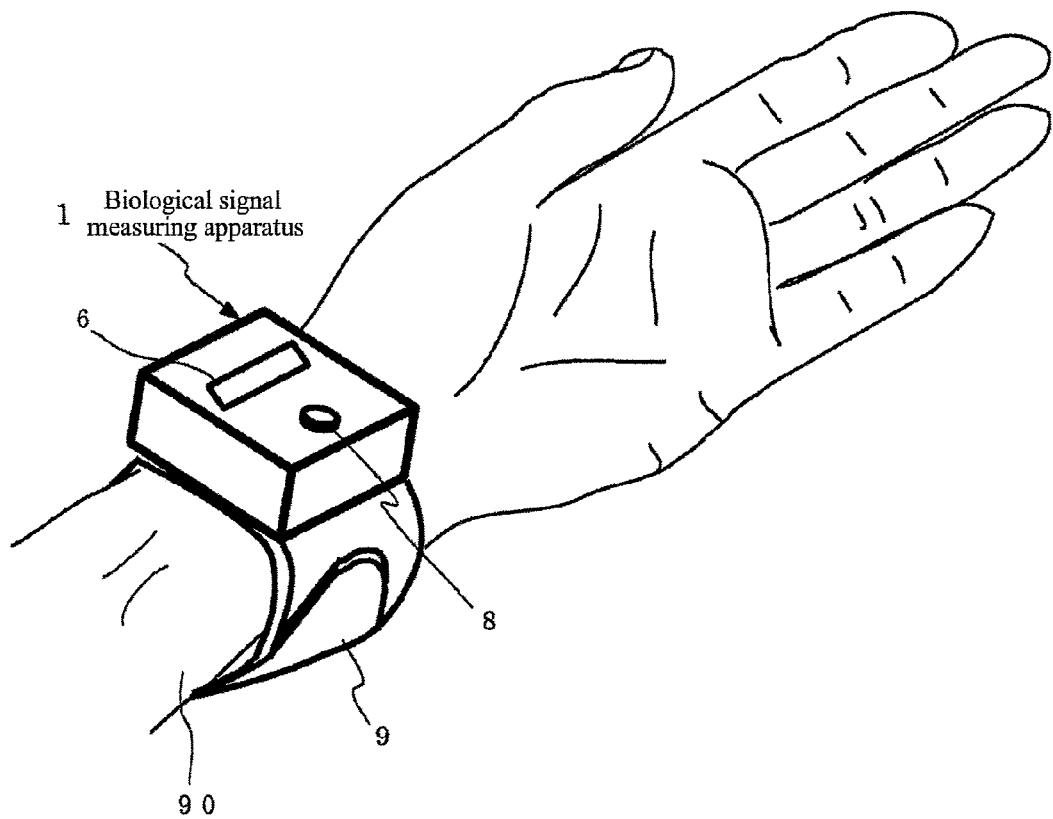
FIG. 4 is an outline view showing a state in which a first embodiment of a biological signal measuring apparatus in accordance with the present invention is worn on a wrist.
Figure 5:
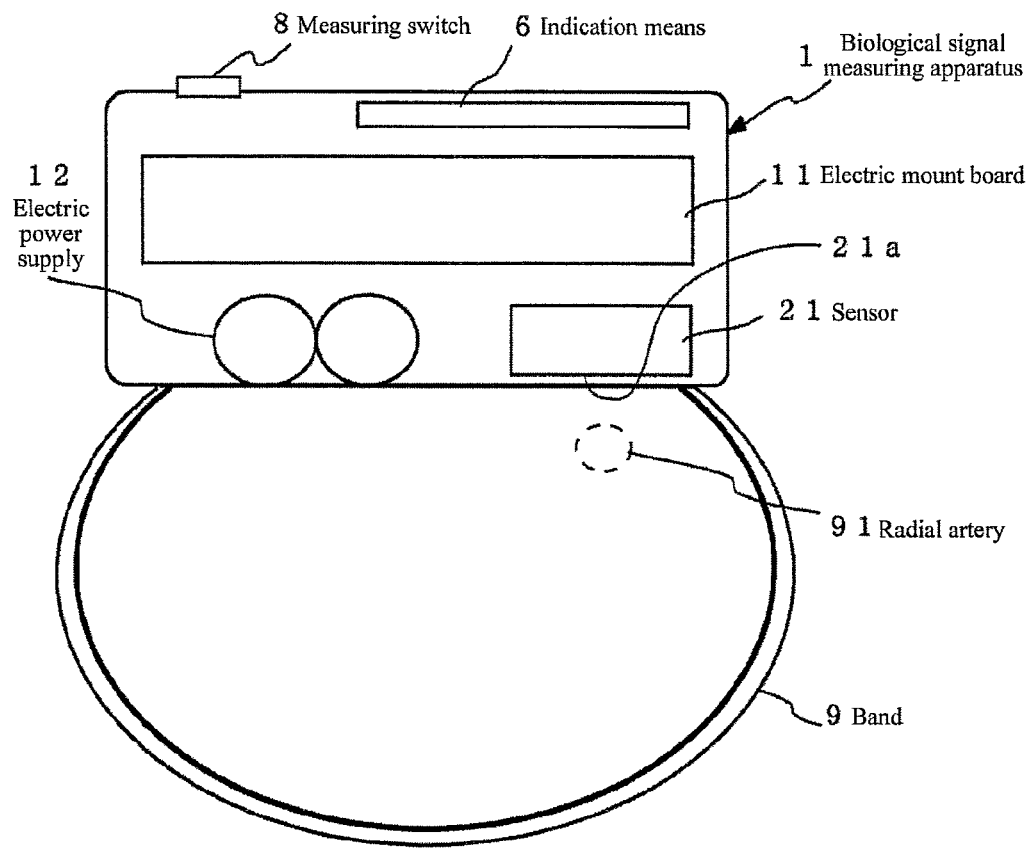
FIG. 5 is a cross sectional view in the case in which a first embodiment of a biological signal measuring apparatus in accordance with the present invention is worn on a wrist.
Figure 6:
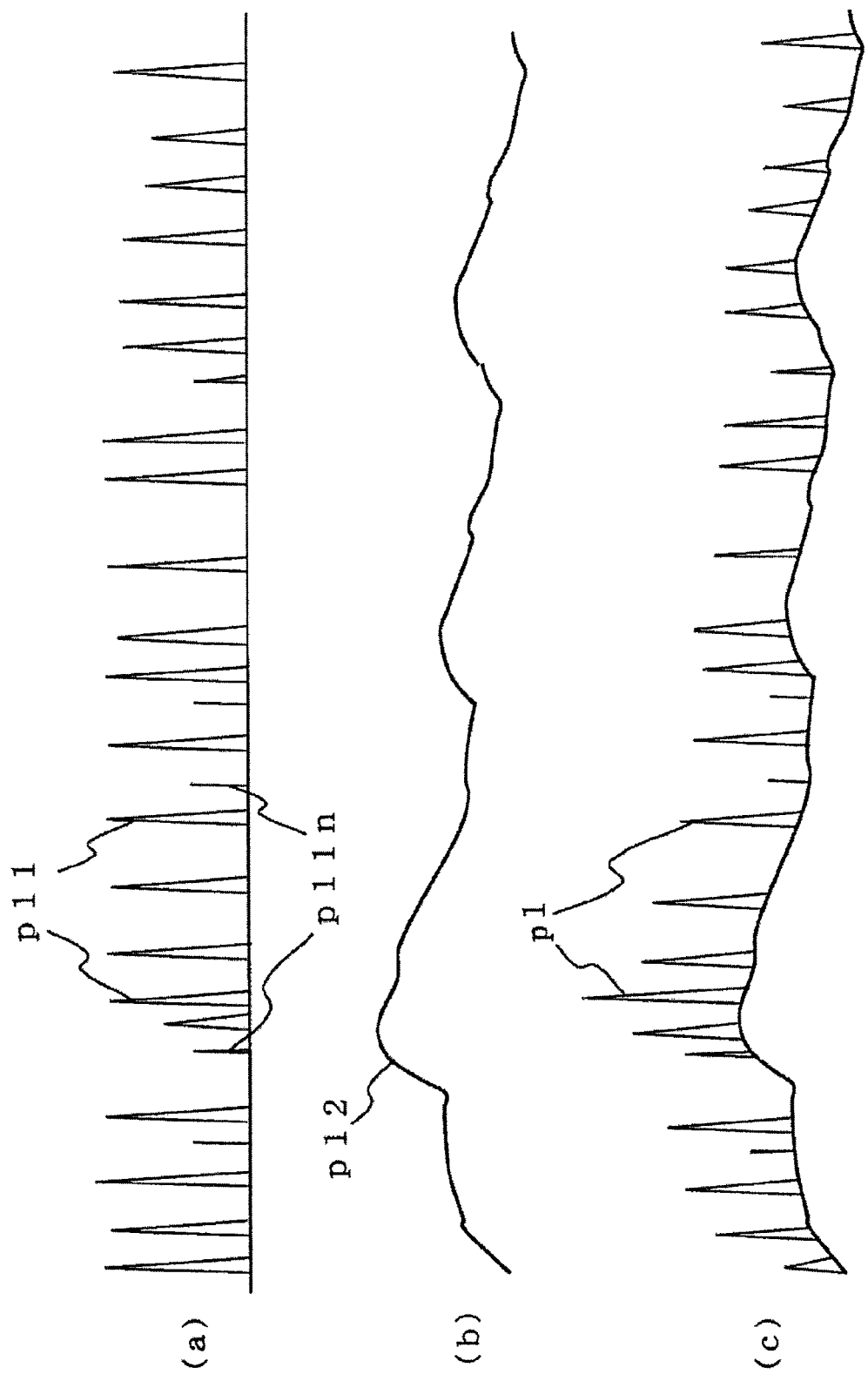
FIG. 6 is a waveform diagram of a general oscillatory wave.
Figure 7:
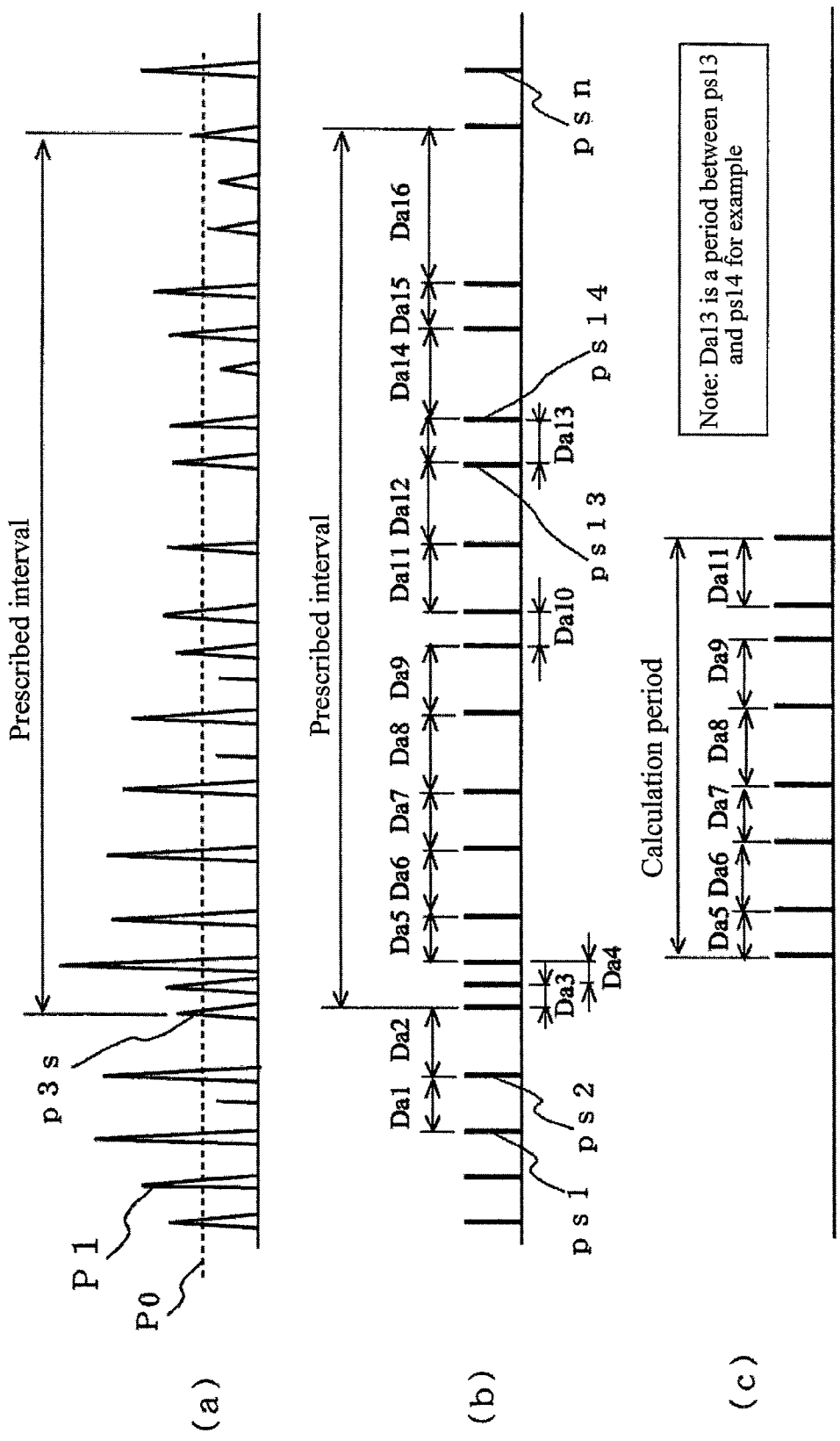
FIG. 7 is a waveform diagram of a general oscillatory wave.

[Descriptions of a Wearing Outline View: FIGS. 3 to 5]

The outline view of a biological signal measuring apparatus 1 will be described with reference to FIG. 3, FIG. 4, and FIG. 5 in the next place. In this example illustrated, the biological signal measuring apparatus in accordance with the present invention is worn on a human body and is operated as an apparatus that is configured to measure a pulse wave.

FIG. 3 is an outline view showing the biological signal measuring apparatus 1 in accordance with the present invention. FIG. 4 is an outline view showing a state in which the biological signal measuring apparatus in accordance with the present invention is worn on a wrist. FIG. 5 is a cross sectional view in the case in which the biological signal measuring apparatus 1 in accordance with the present invention is worn on a wrist part.

As shown in FIG. 3, the biological signal measuring apparatus 1 has a size slightly larger than a wristwatch, and is provided with a flexible band 9 in such a manner that the biological signal measuring apparatus 1 can be conveniently worn on a wrist. The band 9 can be in a ring shape, or can be in a C shape having an open end at a part. The band 9 can also be provided with a mechanism for adjustment in such a manner that a shape or an inner diameter of the band 9 can be modified.

It is convenient that the measuring switch 8 that is an operation button for starting a measurement is disposed at a position that can be easily seen and that enables an operation to be carried out easily in such a manner that the biological signal measuring apparatus 1 can be easily operated even in a physical exercise. Similarly, the indication means 6 is disposed on a front face of a body, and a user can easily check the number of pulses that have been measured. For the example shown in FIG. 3, the displayed number of pulses is 112.

As shown in FIG. 4, the biological signal measuring apparatus 1 is worn on a wrist 90 with the band 9 and close to a radial artery in such a manner that the sensor 21 that is mounted on a rear face of the biological signal measuring apparatus 1 can easily detect a pulse wave that is an oscillatory wave and the indication means 6 is disposed on an upward trend from a face of a palm of a hand.

FIG. 5 is a cross sectional view schematically showing the biological signal measuring apparatus 1 in the case in which the biological signal measuring apparatus 1 is viewed in a direction of an elbow from fingers of a hand. An electric mount board 11 that configures a circuit is mounted inside the biological signal measuring apparatus 1, and is connected to the measuring switch 8, the indication means 6, the sensor 21, and the electric power supply 12 by using a wire not shown. A symbol 21a represents a detection face of the sensor 21.

As described earlier, a pressure sensor can be used as the sensor 21. The sensor 21 is provided with a detection face 21a, and detects a pressure that is applied to the detection face 21a.

In the case in which the biological signal measuring apparatus 1 is worn on a biological body, a position of the biological signal measuring apparatus 1 is adjusted by using the band 9 in such a manner that the detection face 21a of the sensor 21 overlaps on a radial artery 91 inside the wrist 90 in a planar pattern.

The biological signal measuring apparatus 1 is provided with the sensor 21 on the rear face thereof. Consequently, it is convenient that the position of the sensor 21 of the biological signal measuring apparatus 1 is designed in advance in such a manner that the sensor 21 is abutted to a skin over the radial artery 91 in the ordinary course of events in the case in which the biological signal measuring apparatus 1 is worn on the wrist 90.

Figure 10:
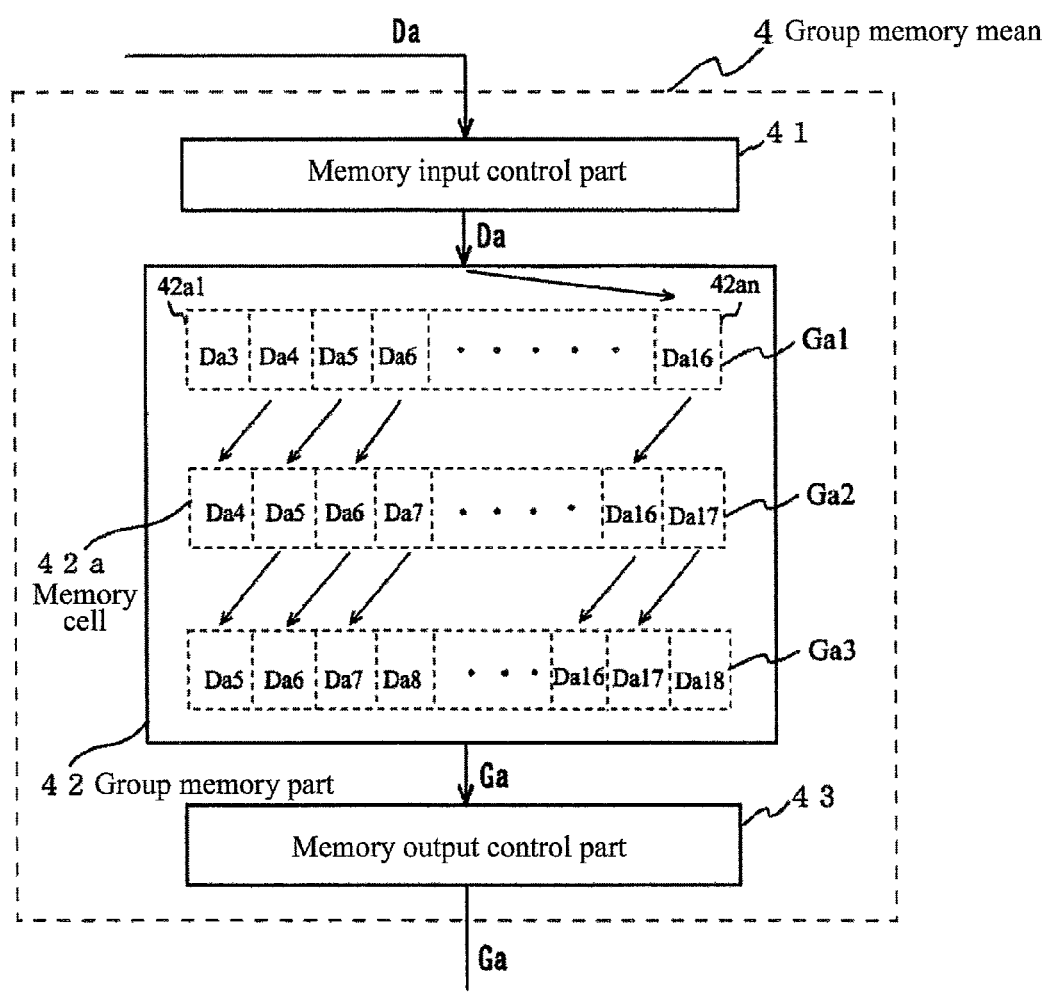
FIG. 10 is a block diagram for illustrating a group memory means for a second embodiment of a biological signal measuring apparatus in accordance with the present invention.
Figure 11:
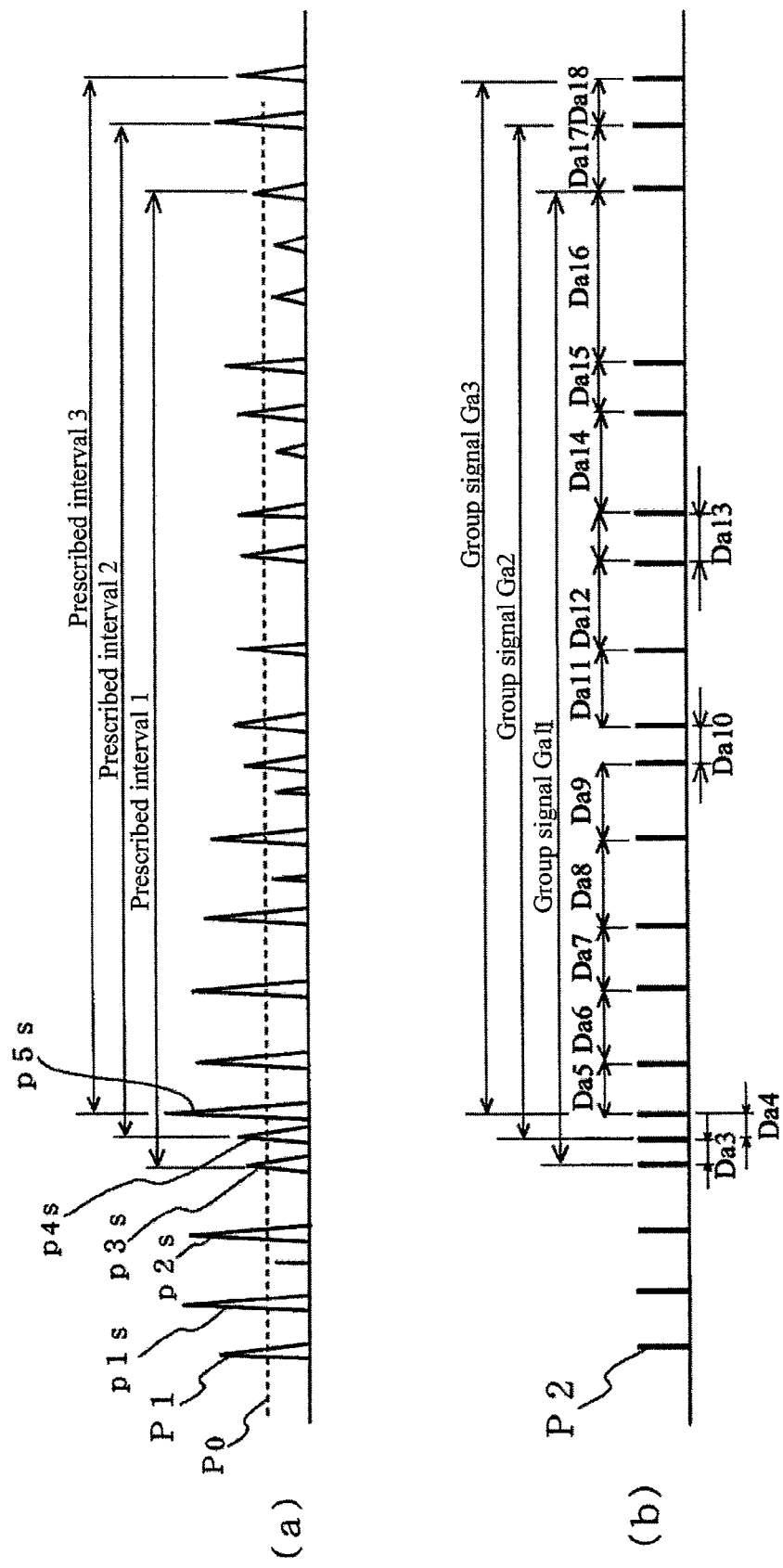
FIG. 11 is a waveform diagram of an oscillatory wave signal for a second embodiment of a biological signal measuring apparatus in accordance with the present invention.
Figure 12:
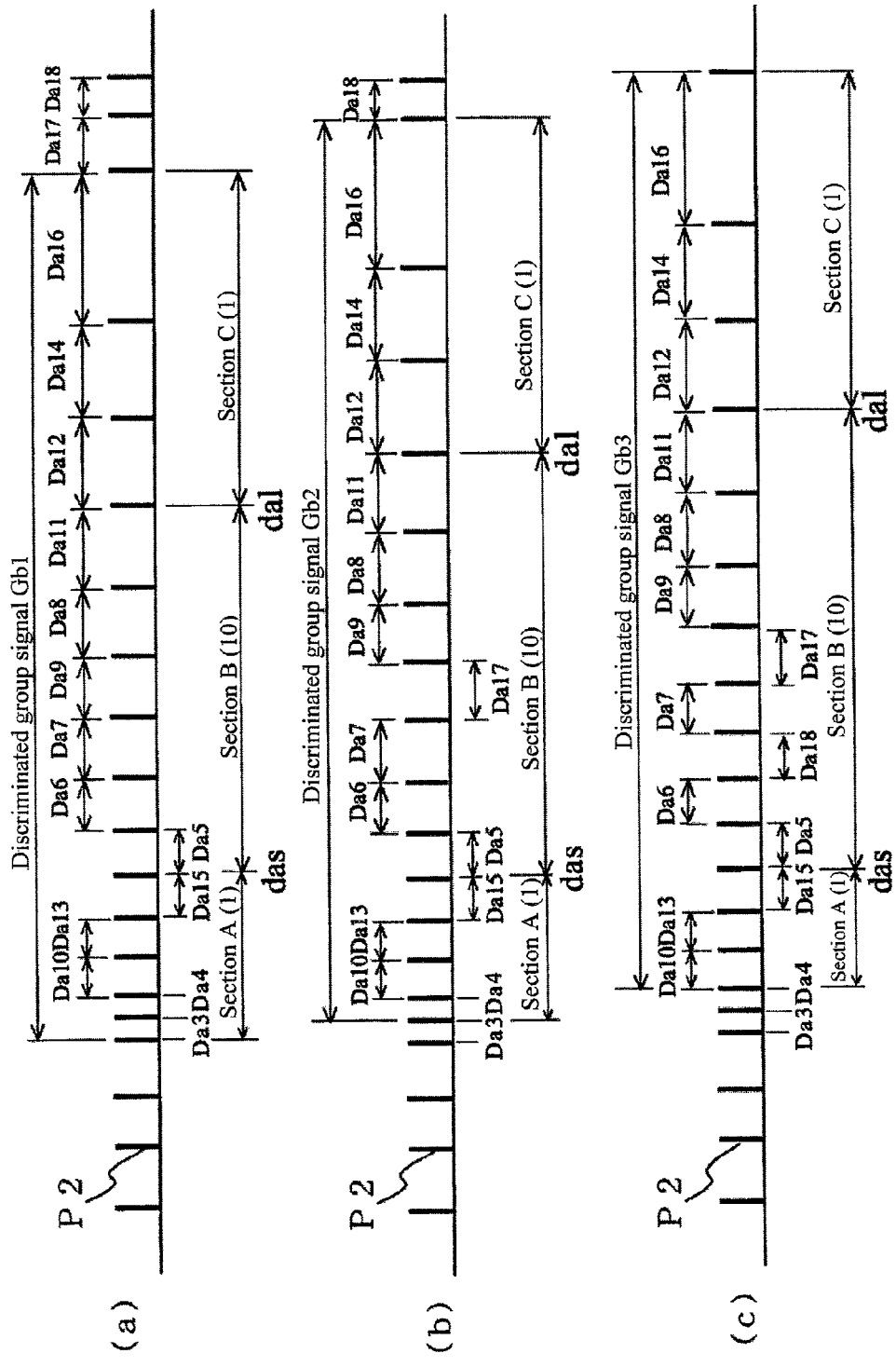
FIG. 12 is a waveform diagram of an oscillatory wave signal for a second embodiment of a biological signal measuring apparatus in accordance with the present invention.

[Embodiment 2]
[Descriptions of all Drawings for a Second Embodiment: FIG. 10, FIG. 11, and FIG. 12]

A second embodiment (example) of the biological signal measuring apparatus in accordance with the present invention will be described below in detail with reference to FIG. 10, FIG. 11, and FIG. 12. For the second embodiment, a configuration of a group memory means is different from that of the first embodiment. FIG. 10 is a block diagram for illustrating a group memory means for the second embodiment of the biological signal measuring apparatus in accordance with the present invention. FIG. 11 is a waveform diagram of an oscillatory wave signal for the second embodiment of the biological signal measuring apparatus in accordance with the present invention. FIG. 12 shows the results of sectioning the oscillatory wave signal of FIG. 11. For the descriptions, refer to the functional block diagram of FIG. 1 showing the first embodiment together with the above figures.

A difference of the second embodiment from the first embodiment is that only one or a few of periodic data Da is rewritten on time series, whereby an update of an indication of a vibration frequency can be enabled in a short time, without rewriting all of periodic data Da in updating the group signal Ga.

More specifically, in the case in which the sensor signal P1 that has been calculated from a pulse wave measured in a serial manner is processed, a method in which the next "prescribed interval" is processed after a processing of a signal in one "prescribed interval" is completed is not adopted, and signals in a plurality of prescribed intervals are processed in a serial manner.

Every time when a new oscillatory wave signal P2 is generated from the sensor signal P1 that has been measured in a serial manner, the new periodic data Dan is incorporated, a new group signal Gan is formed, and the new vibration frequency data Dbn is calculated. Such a method is a processing based on a so-called moving average method.

In the first place, the configuration will be described with reference to the block diagram of FIG. 10.

As shown in FIG. 10, a group memory means in accordance with the second embodiment has a configuration of a partial update type in which the new periodic data Dan is incorporated and a new group signal Gan is formed every time when a new oscillatory wave signal P2 is generated as described above, whereby a prescribed interval is partially updated every time when a new oscillatory wave signal P2 is generated.

Although three memory cells 42a are shown for descriptions in FIG. 10, one memory cell 42a is used to update the contents in the embodiment. Needless to say, three memory cells 42a can also be used.

The operations will be described in the next place.

FIG. 11 is a waveform diagram of an oscillatory wave signal for the second embodiment of the biological signal measuring apparatus in accordance with the present invention. FIG. 11(a) shows the sensor signal P1 that represents a general oscillatory wave, that is, a pulse wave similarly to the first embodiment, and indicates that a range of the "prescribed interval" is a target to be measured. For the "prescribed interval", the prescribed interval 1, the prescribed interval 2, and the prescribed interval 3 are shown in the figure.

As described earlier, the "prescribed interval" is a range for calculating the number of pulses in a certain period of time from a plurality of sensor signals P1. The "prescribed interval" can be started with any sensor signal P1 calculated from a pulse wave that has been measured in a serial manner. As a matter of practical convenience for the descriptions, the example shown in FIG. 11 indicates the state in which the prescribed interval 1 is started with a waveform p3s. Similarly, the prescribed interval 2 is started with a waveform p4s, and the prescribed interval 3 is started with a waveform p5s.

The second embodiment is a system in which only one or a few of periodic data Da (periodic data Da3 and periodic data Da4 for instance) that configure the group signal Ga are deleted, and one or a few of new periodic data Da (periodic data Da17 and periodic data Da18 for instance) are stored by way of compensation.

More specifically, as shown in FIG. 11(b), the first group signal Ga1 is formed by a plurality of periodic data Da in the prescribed interval 1, and is transmitted to the vibration frequency calculation means 5.

After that, a new oscillatory wave signal P2 is generated by a new oscillatory wave of a user, and the new periodic data Da is input to the group memory means 4 from the oscillatory wave period measuring part 3. The periodic data Da is data of the prescribed interval 2.

The memory input control part 41 shown in FIG. 10 then deletes the oldest periodic data Dan (that has been stored in the first place) on time series, and transmits the periodic data Dan+1 that has been stored in the second place on time series to a memory part that has stored the oldest periodic data Dan on time series ("Dan+1" is the (n+1)th Da, and a similar expression will be used in the following).

Moreover, the third periodic data Dan+3 is transmitted to a memory part that has stored the second periodic data Dan+2 on time series, and a similar shift operation is repeated a plurality of times. A plurality of periodic data Dan+1 to Dam including the latest periodic data Dam on time series are then collected in the order of time series, and are stored into the memory cell 42a of the group memory part 42 shown in FIG. 10 as the second group signal Ga2.

In the case in which the second group signal Ga2 is stored into the memory cell 42a of the group memory part 42, the memory output control part 43 outputs the second group signal Ga2 to the vibration frequency calculation means 5. The vibration frequency calculation means 5 then calculates the second vibration frequency data Db2 by the weighted average method based on the second group signal Ga2.

Similarly in the following, after the second group signal Ga2 is formed and transmitted to the vibration frequency calculation means 5, a new oscillatory wave signal P2 is generated by a new oscillatory wave of a user. In the case in which the new periodic data Da is then input to the group memory means 4 from the oscillatory wave period measuring part 3 (the periodic data Da is data of the prescribed interval 3), the periodic data Da is stored as the new group signal Ga3 according to the above described shift operation.

In the case in which the third group signal Ga3 is stored into the memory cell 42a of the group memory part 42, the memory output control part 43 outputs the third group signal Ga3 to the vibration frequency calculation means 5. The vibration frequency calculation means 5 then calculates the third vibration frequency data Db3 by the weighted average method based on the third group signal Ga3.

The above conditions are shown in FIG. 12. FIG. 12(a) shows the group signal Gb1 in which the sectioning of the periodic data Da has been completed based on the prescribed interval 1. Similarly, 12(b) shows the group signal Gb2 in which the sectioning of the periodic data Da has been completed based on the prescribed interval 2, and 12(c) shows the group signal Gb3 in which the sectioning of the periodic data Da has been completed based on the prescribed interval 3.

For rewriting of the periodic data Da that configure the group signal Ga, it is possible as a matter of course to rewrite not only one periodic data Da but also two, three, or more periodic data Da corresponding to the required contents to the performance of the biological signal measuring apparatus 1, such as that a speed of a measurement is of importance or an accuracy of measurement is of importance for a measurement of an oscillatory wave.

[Detailed Description of Advantageous Effects of the Invention]

The advantageous effects of the second embodiment described above will be summarized in the following.

As described above, rewriting of the group signal Ga is carried out by one or a few of new periodic data Da, and every time a calculation and an indication of the vibration frequency data Db are carried out in each case.

This is the extremely useful technology in the case in which the performance requirement to the biological signal measuring apparatus 100 is an immediacy of an indication.

[Summary of the Entire Descriptions]

As described above, by the biological signal measuring apparatus in accordance with the present invention, after a plurality of periodic data Da are collected as the group signal G, the plurality of periodic data Da are compared with the predetermined lengths das and dal of the periodic signal to be discriminated as a plurality of sections and to be stored for each section. A weight coefficient is increased for the periodic data Da of the section B, that is, a section of a middle period, and a weight coefficient is decreased for the periodic data Da of the section A, that is, a section of a short period and the periodic data Da of the section C, that is, a section of a long period to carry out the weighted average calculation.

Consequently, in handling a signal and a noise, a distinction is not made too sharp between a signal and a noise as 1 or 0, and a signal and a noise are individually weighted sensitively in detail. As a result, a reduction in the number of data to be measured does not cause a frequency band to be expanded, whereby it is possible to provide the biological signal measuring apparatus having a high degree of accuracy.

Moreover, in the case of the second embodiment described, it is possible to provide the biological signal measuring apparatus having an excellent immediacy of an indication.

While the preferred embodiments in accordance with the present invention have been described above, the present invention is not restricted to the embodiments, and various changes, modifications, and functional additions can be thus made without departing from the scope of the present invention.

INDUSTRIAL APPLICABILITY

The present invention is suitable for the healthcare equipment such as a heart rate measuring instrument since a measurement of an oscillatory wave that is generated by a biological body can be carried out in a proper manner in the case in which a disturbance noise or a body motion noise is large in a measurement during an exercise. Moreover, the present invention can be applied to not only a measuring instrument for a biological body but also a measuring instrument of a physical quantity in an industrial world and an analytical instrument of data based on a periodic phenomenon.

EXPLANATION OF LETTERS OR NUMERALS

1: Biological signal measuring apparatus
2: Oscillatory wave detection means
21: Sensor
21a: Sensor detection plane
22: Oscillatory wave detection part
23: Reference value signal memory par
3: Oscillatory wave period measuring part
4: Group memory means
41: Memory input control part
42: Group memory part
42a: Memory cell
43: Memory output control part
5: Vibration frequency calculation means
51: Section discrimination part
52: Section memory part
53: Weight coefficient memory part
54: Oscillatory wave period weighted average value calculation part
55: Vibration frequency calculation part
6: Indication means
7: Clock generation part
8: Measuring switch
9: Band
90: Wrist
91: Radial artery
10: Microprocessor
11: Electric mount board
12: Electric power supply
14: Memory device
P0: Reference value signal
P1: Sensor signal
p1: Sensor internal signal
p11n: Noise component
p12: Fluctuation noise
P2: Oscillatory wave signal
Da: Periodic data
Da1: Periodic data that is oldest on time series
Da2: Periodic data that is second oldest on time series
Da3: Periodic data that is third oldest on time series
Dan, Dam: Periodic data that is latest on time series
Dan+1: Periodic data next to the periodic data Dan on time series
Ga: Group signal
Gb: Discriminated group signal
Dc: Section data Dca: Section A data
Dcb: Section B data
Dcc: Section C data
K: Weight coefficient
Ka: Weight coefficient of the section A
Kb: Weight coefficient of the section B
Kc: Weight coefficient of the section C
Dd: Oscillatory wave period weighted average value
Db: Vibration frequency data
C: Clock signal
XA: Sum of periodic data Da of the section A data Dca
XB: Sum of periodic data Da of the section B data Dcb
XC: Sum of periodic data Da of the section C data Dcc
XAn: Number of data of the section A data Dca
XBn: Number of data of the section B data Dcb
XCn: Number of data of the section C data Dcc
fc: Cutoff frequency
M: Averaging point
Δt: Sample interval
C: −3 db point constant

What is claimed is:

1. A biological signal measuring apparatus configured to detect an oscillatory wave that is generated by a biological body and to calculate data of the vibration frequency per unit time, comprising:
a pressure sensor, configured to detect an oscillatory wave that is generated by a biological body as a sensor signal and to output the sensor signal having an amplitude that is larger than an amplitude of a reference value signal as an oscillatory wave signal;
an oscillatory wave period measuring part configured to measure a time interval of the oscillatory wave signals and to output periodic data;
a group memory means configured to collect a plurality of the periodic data and to store the plurality of the periodic data as a group signal that is a data group to be measured; and
a vibration frequency calculation means configured to calculate data of the vibration frequency based on the group signal that has been stored into the group memory means,
wherein the vibration frequency calculation means comprises:
a section discrimination part configured to input the plurality of periodic data that configure the group signal and to compare the plurality of periodic data and a length of a predetermined periodic signal to carry out a section discrimination;
a section memory part configured to store the plurality of periodic data to which a section discrimination has been carried out by the section discrimination part for each section and to output section data for a plurality of sections;
a weight coefficient memory part configured to store a plurality of weight coefficients, defined by a size of an anticipated body motion noise, that correspond to the plurality of section data; and
an oscillatory wave period weighted average value calculation part configured to calculate an oscillatory wave period weighted average value from the plurality of section data and the plurality of weight coefficients corresponding to the section data,
wherein data of the vibration frequency is calculated based on the oscillatory wave period weighted average value.

2. The biological signal measuring apparatus according to claim 1, wherein:
the section discrimination part is configured to calculate a length of the predetermined periodic signal based on the plurality of periodic data.

3. The biological signal measuring apparatus according to claim 2, further comprising an indication means configured to indicate the data of the vibration frequency.

4. The biological signal measuring apparatus according to claim 1, further comprising an indication means configured to indicate the data of the vibration frequency.

5. The biological signal measuring apparatus according to claim 1, wherein all periodic data are rewritten for an update in the case in which a group signal that is stored into the group memory means is updated.

6. The biological signal measuring apparatus according to claim 1, wherein a part of periodic data is rewritten for an update in the case in which a group signal that is stored into the group memory means is updated.

7. The biological signal measuring apparatus according to claim 1, wherein the oscillatory wave is a pulse wave that is generated by the pulsation of a heart, an electrocardiographic wave that indicates an electrical activity of a heart, a skin oscillatory wave that is generated by a breath, an oscillatory wave in walking, or a brain wave.

8. A biological signal measuring method for detecting an oscillatory wave that is generated by a biological body and for calculating data of the vibration frequency per unit time, comprising:
an oscillatory wave signal generation step for detecting an oscillatory wave that is generated by a biological body as a sensor signal using a pressure sensor, and for generating the sensor signal having an amplitude that is larger than an amplitude of a reference value signal as an oscillatory wave signal;
an oscillatory wave period data generation step for generating periodic data from a time interval of the oscillatory wave signals;
a group signal generation step for collecting a plurality of the periodic data and for generating a group signal that is a data group to be measured; and
a vibration frequency calculation step for calculating data of the vibration frequency based on the group signal,
wherein the vibration frequency calculation step comprises:
a section discrimination step for comparing the plurality of periodic data and a length of a predetermined periodic signal to carry out a section discrimination based on the plurality of periodic data that configure the group signal;
a section data generation step for generating section data for a plurality of sections based on the plurality of periodic data to which a section discrimination has been carried out in the section discrimination step; and
an oscillatory wave period weighted average value calculation step for calculating an oscillatory wave period weighted average value from the plurality of section data and a plurality of weight coefficients, defined by a size of an anticipated body motion noise, that correspond to the plurality of section data,
wherein data of the vibration frequency is calculated based on the oscillatory wave period weighted average value.

* * * * *

UNITED STATES PATENT AND TRADEMARK OFFICE
CERTIFICATE OF CORRECTION

| | |
|---|---|
| PATENT NO. | : 9,011,343 B2 |
| APPLICATION NO. | : 12/730630 |
| DATED | : April 21, 2015 |
| INVENTOR(S) | : Hideki Shimizu |

It is certified that error appears in the above-identified patent and that said Letters Patent is hereby corrected as shown below:

In the Claims

Column 21, Line 26, Claim 1, delete "sensor," and insert -- sensor --

Signed and Sealed this
Fifteenth Day of September, 2015

Michelle K. Lee
*Director of the United States Patent and Trademark Office*